(12) United States Patent
Veldhuis-Stribos et al.

(10) Patent No.: US 6,509,179 B1
(45) Date of Patent: Jan. 21, 2003

(54) CONTINUOUS PROCESS FOR PREPARING LACTIC ACID

(76) Inventors: Barbara I. Veldhuis-Stribos, Arkelse Onderweg 93, 4206 AG Gorinchem (NL); Wim J. Groot, Van Ravesteynerf 46, 3315 DH Dordrecht (NL); Brenda M. Dierdorp, Roggeakker 6, 5236 VE Empel (NL); Jan Van Breugel, Middlevaart 48, 4285 WS Woudrichem (NL); Paul L. McWilliams, Renessen LLC, Suite 300 South, 3000 Lakeside Dr., Banockburn, IL (US) 60015; Jeff J. Malsam, 2301 Crosby Rd., Wayzata, MN (US) 55391; Rod R. Fisher, 2301 Crosby Rd., Wayzata, MN (US) 55391; Scott McElmury, PGLA1, 650 Industrial Rd., Blair, NE (US) 68008

( * ) Notice: Subject to any disclaimer, the term of this patent is extended or adjusted under 35 U.S.C. 154(b) by 0 days.

(21) Appl. No.: 09/689,493

(22) Filed: Oct. 12, 2000

(51) Int. Cl.$^7$ ................................................ C12P 7/56
(52) U.S. Cl. ..................................................... 435/139
(58) Field of Search ........................................ 435/139

(56) References Cited

U.S. PATENT DOCUMENTS

| | | | |
|---|---|---|---|
| 686,170 A | 11/1901 | Waite ........................... | 562/580 |
| 1,160,595 A | 11/1915 | Gruter et al. ................. | 560/179 |
| 1,668,806 A | 5/1928 | Gabriel et al. ............... | 560/179 |
| 1,906,068 A | 4/1933 | Jenemann .................... | 562/580 |
| 2,097,725 A | 11/1937 | Gay .............................. | 62/192 |
| 2,134,361 A | 10/1938 | French ........................ | 366/113 |
| 2,223,797 A | 12/1940 | Tindall ........................ | 562/580 |
| 2,327,191 A | 8/1943 | Kane ........................... | 435/145 |
| 2,420,234 A | 5/1947 | Filachione ................... | 560/179 |
| 2,464,487 A | 3/1949 | Chappell ..................... | 285/55 |
| 2,539,472 A | 1/1951 | Ratchford ................... | 562/580 |
| 2,581,452 A | 1/1952 | Solomon ..................... | 518/724 |
| 2,650,248 A | 8/1953 | Collier ........................ | 562/593 |
| 2,664,441 A | 12/1953 | Owens et al. ............... | 548/534 |
| 2,697,724 A | 12/1954 | Collier ........................ | 562/513 |
| 2,710,880 A | 6/1955 | Filachione et al. .......... | 562/580 |
| 2,712,516 A | 7/1955 | Kool et al. .................. | 435/139 |
| 2,880,179 A | 3/1959 | Comar ........................ | 252/364 |
| 3,030,276 A | 4/1962 | Thomsen .................... | 435/145 |
| 3,944,606 A | 3/1976 | Rieger ........................ | 562/584 |
| 4,013,508 A | 3/1977 | Zangrandi et al. ........... | 435/42 |
| 4,250,331 A | 2/1981 | Shimshick ................... | 562/485 |
| 4,275,234 A | 6/1981 | Baniel et al. ................ | 562/584 |
| 4,282,323 A | 8/1981 | Yates .......................... | 435/140 |
| 4,323,702 A | 4/1982 | Kawabata et al. ........... | 562/485 |
| 4,334,095 A | 6/1982 | Baniel ......................... | 562/584 |
| 4,405,717 A | 9/1983 | Urbas .......................... | 435/140 |
| 4,444,881 A | 4/1984 | Orbas .......................... | 435/139 |
| 4,698,303 A | 10/1987 | Bailey et al. ................ | 435/139 |
| 4,705,894 A | 11/1987 | Su et al. ...................... | 562/580 |
| 4,720,579 A | 1/1988 | Kulprathiapanja .......... | 562/580 |
| 4,771,001 A | 9/1988 | Bailey et al. ................ | 435/139 |
| 4,855,494 A | 8/1989 | Margureanu et al. ....... | 562/580 |
| 4,877,731 A | 10/1989 | Ling et al. ................... | 435/142 |
| 4,924,027 A | 5/1990 | Kulprathipanja et al. ... | 562/580 |
| 4,963,486 A | 10/1990 | Hang ........................... | 435/139 |
| 4,994,609 A | 2/1991 | Baniel et al. ................ | 562/580 |
| 5,002,881 A | 3/1991 | Van Nispen et al. ........ | 435/139 |

(List continued on next page.)

FOREIGN PATENT DOCUMENTS

| | | |
|---|---|---|
| AT | B 379582 | 1/1986 |
| CA | A 581194 | 8/1959 |
| DE | A 678373 | 7/1939 |

(List continued on next page.)

OTHER PUBLICATIONS

R. Blumberg et al., "Interesting Aspects in the Development of a Novel Solvent Extration Process for Producing Sodium Bicarbonate," Proceedings of the International Solvent Extraction Conference, pp. 2789–2802, col. 3, issued 1974.
N.L. Ricker, "Solvent Extraction with Amines for Recovery of Acetic Acid from Dilute Aqueous Industrial Streams," J. Separa. Proc. Technol. 1(2) 23–90 (1980).

Primary Examiner—Herbert J. Lilling
(74) Attorney, Agent, or Firm—Coudert Brothers LLP

(57) ABSTRACT

The invention relates to a continuous process for preparing lactic acid, comprising:

(a) acidifying an aqueous feed, which has been obtained by fermentation and mainly contains lactate, with a stream containing inorganic acid to a pH of from 1 to 4 to form an aqueous stream which mainly consists of lactic acid and a salt, (b) removing the salt from the aqueous stream which mainly contains lactic acid and salt to form a first aqueous stream which mainly contains lactic acid, (c) passing the first aqueous stream which mainly contains lactic acid over a column containing activated carbon to form a second aqueous stream which mainly contains lactic acid, (d) subjecting the second aqueous stream which mainly contains lactic acid to a first extraction step, wherein the second aqueous stream which mainly contains lactic acid is brought into contact with a substantially water-insoluble stream which contains an extractant, to form an organic phase which mainly contains lactic acid and extractant and a first water phase which mainly contains impurities, (e) subjecting the organic phase which mainly contains lactic acid and extractant to a second extraction step, wherein the organic phase which mainly contains lactic acid and extractant is brought into contact with an aqueous stream to form a water phase which mainly contains lactic acid and an organic phase which contains extractant, wherein the organic phase which contains extractant is recycled to step (d), and (f) concentrating the water phase which mainly contains lactic acid by means of evaporation of water to form a concentrated lactic acid solution in water.

64 Claims, 2 Drawing Sheets

U.S. PATENT DOCUMENTS

| | | | |
|---|---|---|---|
| 5,023,349 A | 6/1991 | Bhatia | 549/274 |
| 5,023,350 A | 6/1991 | Bhatia | 549/274 |
| 5,034,105 A | 7/1991 | Berglund et al. | 204/538 |
| 5,043,458 A | 8/1991 | Bhatia | 549/274 |
| 5,068,418 A | 11/1991 | Kulprathipanja et al. | 562/580 |
| 5,071,751 A | 12/1991 | Morita | 435/101 |
| 5,071,754 A | 12/1991 | Walkup et al. | 435/135 |
| 5,079,164 A | 1/1992 | Kirkovits et al. | 435/252.5 |
| 5,089,664 A | 2/1992 | Dalcanale et al. | 562/580 |
| 5,104,492 A | 4/1992 | King et al. | 203/15 |
| 5,132,456 A | 7/1992 | King | 562/593 |
| 5,132,458 A | 7/1992 | Honel et al. | 564/367 |
| 5,136,057 A | 8/1992 | Bhatia | 549/274 |
| 5,138,074 A | 8/1992 | Bellis et al. | 549/379 |
| 5,142,023 A | 8/1992 | Gruber et al. | 528/354 |
| 5,143,834 A | 9/1992 | Glassner et al. | 435/145 |
| 5,196,551 A | 3/1993 | Bhatia et al. | 549/274 |
| 5,198,086 A | 3/1993 | Chlauda et al. | 204/182.4 |
| 5,210,294 A | 5/1993 | Mantovani et al. | 562/580 |
| 5,210,296 A | 5/1993 | Cockrem et al. | 562/589 |
| 5,231,225 A | 7/1993 | Baniel et al. | 562/513 |
| 5,245,078 A | 9/1993 | Maeda et al. | 562/580 |
| 5,250,159 A | 10/1993 | Butterworth | 204/98 |
| 5,264,614 A | 11/1993 | Brake | 560/179 |
| 5,352,825 A | 10/1994 | Feldman et al. | 562/580 |
| 5,420,304 A | 5/1995 | Verser et al. | 549/274 |
| 5,426,219 A | 6/1995 | Lehnhardt et al. | 562/580 |
| 5,426,220 A | 6/1995 | Baniel et al. | 562/580 |
| 5,453,365 A | 9/1995 | Sterzel et al. | 435/135 |
| 5,488,156 A | 1/1996 | Kulprathipanja et al. | 562/580 |
| 5,510,526 A | 4/1996 | Baniel et al. | 562/580 |
| 5,641,406 A | 6/1997 | Sarhaddar et al. | 210/656 |
| 5,759,826 A | 6/1998 | Ahelers | 435/136 |
| 5,766,439 A | 6/1998 | Eyal et al. | 204/524 |
| 5,773,653 A | 6/1998 | Baniel | 562/580 |
| 5,780,276 A | 7/1998 | Baniel | 435/136 |
| 5,786,185 A | 7/1998 | Tsao et al. | 435/139 |
| 5,801,025 A | 9/1998 | Ohara et al. | 435/139 |
| 5,831,122 A | 11/1998 | Eyal | 562/580 |
| 5,932,455 A | 8/1999 | Viljava | 435/139 |
| 6,229,046 B1 | 5/2001 | Eyal et al. | 562/589 |

FOREIGN PATENT DOCUMENTS

| | | |
|---|---|---|
| DE | A 1268088 | 5/1968 |
| DE | A 3222837 | 12/1983 |
| DE | A 206373 | 1/1984 |
| DE | A 3506944 | 10/1985 |
| EP | A 135728 | 4/1985 |
| EP | A 159585 | 10/1985 |
| EP | A 393818 | 2/1990 |
| EP | A 614983 | 3/1994 |
| GB | A 146411 | 10/1921 |
| GB | A 907321 | 10/1962 |
| GB | A 1004218 | 9/1965 |
| IL | 33552 | 12/1969 |
| JP | A 46/30176 | 9/1971 |
| JP | A 57-2473 | 1/1982 |
| JP | A 7118523 | 12/1995 |
| JP | A 8164541 | 6/1996 |
| JP | A 3005172 | 1/2000 |
| WO | WO 93/004400 | 1/1993 |
| WO | WO 93/06226 | 4/1993 |
| WO | WO 95/32301 | 11/1995 |
| WO | WO 98/15517 | 4/1998 |
| WO | WO 98/15519 | 4/1998 |
| WO | WO 98/37050 | 8/1998 |
| WO | WO 98/55442 | 12/1998 |

CONTINUOUS PROCESS FOR PREPARING LACTIC ACID

FIELD OF THE INVENTION

The present invention relates to a continuous process for preparing lactic acid from an aqueous feed which has been obtained by fermentation and mainly contains lactate. The term "a feed which mainly contains lactate" refers to a feed which contains about 250 g of lactate ion/l or less, based on the total amount of the feed, at least 90 wt % of the lactate ion being present as free lactate ion and the remaining quantity of the lactate ion being present as undissociated acid.

BACKGROUND OF THE INVENTION

Many methods are known from the prior art. WO 99/19290, published on Apr. 22, 1999, describes various methods for purifying lactic acid from an aqueous composition of lactic acid and a salt of lactic acid (a lactate) dissolved therein, the aqueous composition having been obtained by fermentation of a suitable feed at a pH of 4.8 or less (claim 1). The pH of the aqueous composition is therefore moderately to strongly acidic, so that the composition contains a substantial amount of lactic acid and a substantial amount of lactate. According to page 4, lines 21 to 28 of WO 99/19290, this is actually advantageous, since the lactate after separation of lactic acid can be recycled to the fermentation step where it serves as a buffering agent for controlling the pH during the fermentation. On the other hand, page 14, lines 21 to 30 of WO 99/19290 states that the methods can be implemented using compositions having a pH of at least 0.86 to less than 6.0, which implies that at 25° C., the molar ratio of lactic acid and its salt in these compositions is between 1000: 1 and 0.007:1. Preferably, these compositions have a pH of from 1.98 to 5.00 (molar ratio of lactic acid and its salt is between 75:1 and 0.070:1) and in particular a pH of from 3.0 to 4.5 (molar ratio of lactic acid and its salt is between 7.0:1 and 0.23:1). The lactic acid obtained by the method according to WO 99/19290 is used, in particular, for preparing polylactic acid.

Page 40, line 23, to page 41, line 11, of WO 99/19290 describes a preferred embodiment, wherein a suitable culture medium is fermented to form a composition which contains lactic acid and a lactate. In a subsequent step, the solids are separated by means of, for example, filtration, flocculation, centrifuging or a combination of such techniques, to form an aqueous mixture of lactic acid and lactate. The aqueous mixture of lactic acid and lactate is passed directly to an extraction apparatus, although it is possible for the aqueous mixture to undergo an operation before being passed to the extraction apparatus. Such an operation, for example, is an adjustment of the pH by the addition of an acid such as sulphuric acid, lactate thereby being converted into lactic acid (p. 5, lines 8 to 14 of WO 99/19290). Such an operation would have the drawback, however, of leading to the formation of a waste product consisting, for example, of calcium sulphate (calcium sulphate is formed by the reaction of the lactate formed during the fermentation with sulphuric acid; in the course of the fermentation, for example in the start-up phase, calcium carbonate is then added to maintain the pH of the fermentation medium at a sufficiently high value). Moreover, p. 13, lines 33–36 of WO 99/19290 clearly states that the methods described in this reference are especially suitable for purifying lactic acid from relatively acidic culture media which need not be treated with an acid and which preferably have indeed not undergone such an operation.

According to the above-described preferred embodiment of WO 99/19290, the aqueous mixture of lactic acid and lactate is separated, by means of extraction, into an organic phase which mainly contains lactic acid and an aqueous phase which mainly contains lactate. This extraction can be carried out at a temperature of from 15° C. to 60° C. and atmospheric pressure, and according to p. 28, lines 29 to 32 of WO 99/19290, the organic extractant used comprises a tertiary amine, an oxygen-containing solvent and a hydrocarbon, preferably from 60 to 80% by weight of a tertiary alkylamine such as Alamine 336 (a mixture of trialkylamines having at least 18 carbon atoms, the trialkylamines containing decyl and octyl groups) which is marketed by Henkel Corp., from 5 to 20% by weight of methyl isobutyl ketone and from 10 to 30% by weight of a hydrocarbon such as Isopar K™. Then the organic phase which mainly contains lactic acid is subjected to a back extraction, the lactic acid again being transferred into a polar solvent phase, for example water. This back extraction takes place, for example, at a temperature of from 30° C. to 160° C. or more, and customarily at a temperature of from 90° C. to 160° C. (page 30 lines 26 to 28 of WO 99/19290). According to page 26, lines 22 and 23 of WO 99/19290, this back extraction can also be carried out at a temperature of at least 100° C., for example 150° C. or more, and at a pressure of at least 30 psi(g) (about 2.1 bar). The polar solvent phase which is obtained from the back extraction and which contains lactic acid is then concentrated by means of distillation, either the lactic acid or the polar solvent being separated as a vapour, this being dependent on the respective volatilities. P. 20, lines 15 to 21 of WO 99/19290, describes that such a distillation is preferably carried out at a pressure of less than 300 mmHg (about 0.4 bar), to prevent as far as possible the dimerization and oligomerization of lactic acid. The aqueous phase which is formed in the extraction and mainly contains lactate is recycled (optionally after purification) to the fermentation step. For this method to be feasible and effective, the aqueous mixture of lactic acid and lactate which is purified according to this method must necessarily contain a substantial amount of lactic acid and a substantial amount of lactate. It is therefore necessary for the aqueous mixture of the lactic acid and lactate to be moderately to strongly acidic, for example 4.8 or less. The $pK_a$ of lactic acid is about 3.86 at 25° C., and about 3.89 at 50° C.; see also FIG. 11 of WO 99/19290).

The above-described preferred embodiment of the method for purifying lactic acid has a number of drawbacks. For the purpose of large-scale purification or continuous purification, the extraction should be carried out under carbon dioxide pressure, as described in claim 30 of the U.S. Pat. No. 5,510,526, wherein the partial carbon dioxide pressure is at least 50 psi(g) (about 3.5 bar), relatively expensive equipment being required consequentially which is able to withstand a relatively high pressure. Furthermore, the kinetics of the extraction of the carbon dioxide pressure proves sluggish. It was found that for effective extraction, the contact between the organic phase and the water phase has to be maintained for about 100 hours to reach equilibrium in a stirred system.

Yet another drawback of the abovementioned preferred embodiment is that recycling of the mainly lactate-containing water phase to the fermentation results in accumulation of lactate and impurities in the fermentation. No mass balances are described in WO 99/19290, but it is necessary for part of the aqueous composition of lactic acid and lactate formed during the fermentation to be removed from the fermentation (via a so-called sink or "purge"), which is not described in WO 99/19290, however. The need for a sink or "purge" with a recycling step of this type is described, in contrast, in WO 98/15517 on page 5, last paragraph. WO 98/15517 and WO 99/19290, moreover, come from the same applicant and list the same inventors. The use of a sink or "purge" naturally reduces the yield of the purification. According to the preferred embodiment the throughput is therefore low, and the preferred embodiment has a relatively low yield per unit weight of feed per unit time. The lack of experimental data in WO 99/19290 moreover makes it very difficult for those skilled in the art to reproduce the method described therein.

The extraction under carbon dioxide pressure also gives rise to calcium carbonate. In practice it was found that this calcium carbonate is relatively impure and is short of mineral nutrients and therefore cannot be recycled to the fermentation. This extraction step according to the above-described preferred embodiment therefore gives rise to a waste product, a problem that WO 99/19290 is precisely attempting to prevent. Page 5, lines 3 to 18, describes that the first step of a customary purification of an aqueous composition of lactic acid and lactate comprises the addition of sulphuric acid, calcium sulphate being formed in the process (if calcium carbonate has been used as a pH regulator during the fermentation). Said calcium sulphate is stated to be a waste product. However, it was found that the costs associated with the removal of the waste product calcium sulphate and the procurement of sulphuric acid are considerably lower than the costs associated with the use of carbon dioxide during the extraction step. A further drawback of this method is that a three- or sometimes even a four-phase system is formed (organic phase, water phase, solid phase in the form of calcium carbonate and a gas phase in the form of carbon dioxide), therefore requiring complex and consequently expensive equipment.

Moreover, it was found that in the case of extraction under carbon dioxide pressure, the mainly lactate-containing aqueous phase contains relatively large amounts of lactic acid, so that efficient purification of lactic acid from the aqueous composition obtained from the fermentation requires a recycling step of said aqueous phase. The yield of this preferred embodiment (i.e. (1) fermentation, (2) extraction, (3) back extraction and (4) concentration) of WO 99/19290 is therefore relatively low and provides lactic acid of inadequate purity. Furthermore, said preferred embodiment is either difficult to implement or not sufficiently clearly described in WO 99/19290, especially in view of the lack of experimental data. A further drawback of this method is that it involves a crystallization process (calcium carbonate has to precipitate for the equilibrium to be shifted sufficiently far towards lactic acid), which makes the method highly malfunction-prone. Moreover, the presence of the solid calcium carbonate can easily lead to the formation of emulsions.

WO 98/37050, published on Aug. 27, 1998, describes a method of producing lactic acid and products thereof from a medium which contains an alkaline earth metal lactate, wherein a conjugated base of the alkali metal, obtained from a step carried out previously, is reacted with the medium to form a water-soluble alkali metal lactate and a basic compound of the alkaline earth metal, the separation of the water-soluble alkali metal lactate and the basic compound of the alkaline earth metal, and cleaving the water-soluble alkali metal lactate to form a conjugated base of the alkali metal and a lactic acid product. The lactic acid product can be lactic acid as such, a derivative or a combination of lactic acid and the derivative.

WO 98/15519, published on Apr. 16, 1998, describes a method of recovering purified lactic acid products from an aqueous feed which contains lactic acid, lactate or a mixture thereof, wherein the feed is brought into contact with a substantially immiscible anion exchanger to form a substantially water-immiscible phase which comprises an adduct of the ion exchanger and lactic acid, effecting a condensation reaction in the substantially water-immiscible phase between a carboxyl group of lactic acid and a hydroxyl group, a primary amine group or a secondary amine group to form a lactic acid ester or a lactic acid amide, and the separation of the lactic acid ester or the lactic acid amide from the ion exchanger.

WO 98/15517, published on Apr. 16, 1998, describes a method of recovering lactic acid and products thereof from an aqueous solution which contains lactic acid and a lactate. The method comprises the extraction of at least 70% of lactic acid from the aqueous solution by bringing the solution into contact with a basic extractant to form a lactic acid-containing extract and an aqueous lactate solution, the separation of the lactic acid-containing extract and the aqueous lactate solution, and stripping the lactic acid-containing extract by means of methods known per se. According to a preferred embodiment, the aqueous lactate solution can be acidified, for example with sulphuric acid to form lactic acid and calcium sulphate (waste product), and the lactic acid can then be removed from the aqueous solution, for example by extraction. The extraction step according to WO 98/15517 likewise has to be carried out under carbon dioxide pressure. According to Example 8, this pressure can be 30 atmospheres (about 30 bar). The method according to WO 98/15517 therefore has the drawbacks of calcium carbonate (formed during the extraction carried out under carbon dioxide pressure) and calcium sulphate being formed as waste products, high costs and a relatively low yield and a relatively low throughput.

U.S. Pat. No. 5,766,439, granted on Jun. 16, 1998, describes a method for producing an organic acid such as lactic acid, fermentation giving rise to an aqueous mixture of an organic mono-, di- or tribasic acid having from three to eight carbon atoms. The mixture is admixed with an alkaline earth metal base in such an amount that the pH of the mixture is sufficiently high, a salt of the acid and the alkaline earth metal being formed. The salt of the acid and the alkaline earth metal is then reacted with ammonium ions to form an ammonium salt of the acid. The ammonium salt is then converted into the free acid by means of so-called salt-splitting electrodialysis.

WO 96/01247, published on Jan. 18, 1996, describes a method for recovering a carboxylic acid from an amine-based, water-immiscible solution of an extract which contains an extraction-enhancing agent. An impure aqueous solution of the carboxylic acid is brought into contact with the solution of the extractant, after which the extraction-enhancing agent is extracted from the carboxylic acid-containing extract obtained, by means of an aqueous solution of a salt of the carboxylic acid to form a water phase which contains extraction-enhancing agent and a carboxylic acid-containing extract (organic phase). From the water phase which contains extraction-enhancing agent, the extraction-enhancing agent is removed by means of distillation. The carboxylic acid is recovered from the acid-containing extract by means of back extraction with water. Lactic acid is not mentioned in WO 96/01247.

WO 98/55442 describes a method wherein a solution of lactic acid in water as obtained from fermentation or another source is subjected to at least three steps. The first step comprises the removal of such ionogenic substances from the aqueous solution of lactic acid as are able to catalyse the oligomerization of lactic acid, the solution containing less than 80%, preferably less than 50% and in particular less than 30% of lactic acid. Preferably, an anion exchanger is used to remove cationogenic substances, and a cation exchanger is then used to remove anionogenic substances. The second step comprises concentrating the solution to a concentration of from 50 to 90%, preferably from 70 to 90%, by evaporation at reduced pressure, the pressure being from 50 to 500 mbar and preferably from 50 to 250 mbar and the temperature being kept as low as possible. Preferably, the evaporation is carried out with the aid of flowing-film evaporation. The third step comprises a distillation at a pressure of from 0.001 to 100 mbar, preferably from 0.1 to 20 mbar and in particular from 1 to 10 mbar, the temperature of the wall of the evaporation apparatus being from 80 to 160° C. and preferably from 110 to 160° C. The distillation is preferably carried out with the aid of a mechanically agitated thin-film evaporator or a short-path evaporator and provides pure lactic acid. Optionally, a postconcentration step can be carried out between the second and the third step. This postconcentration is likewise preferably carried out by means of a mechanically agitated thin-film evaporator or a short-path evaporator at a pressure of from 10 to 500 mbar, preferably from 50 to 250 mbar, and at a temperature of from 50 to 150° C., preferably from 80 to 120° C. It is claimed that in the course of said postconcentration the concentration of the solution as obtained from the first concentration step (step two) can be increased to 100% of lactic acid. A drawback of this method is that in the course of the first concentration step (step two) a poor separation is effected between the concentrated lactic acid-containing solution and the mainly water-containing fraction, so that the mainly water-containing fraction contains a considerable amount of lactic acid and impurities such as oligomers of lactic acid, which is deleterious to the efficiency of the method. Moreover, said water-containing fraction must be purified before it can be discharged or be recycled into the method.

Further methods of preparing and purifying an organic acid such as lactic acid or citric acid by means of fermentation are described, for example, in WO 95/32301, WO 93/06226 (lactic acid), WO 93/00440 (lactic acid), U.S. Pat. No. 3,944,606 (citric acid), U.S. Pat. No. 4,275,234 (citric acid, lactic acid, oxalic acid and phosphoric acid), U.S. Pat. No. 5,132,456 (lactic acid, fumaric acid, succinic acid, maleic acid, adipic acid, itaconic acid, benzoic acid and salicylic acid), U.S. Pat. No. 5,510,526 (lactic acid), U.S. Pat. No. 5,766,439 (lactic acid), EP A 159,585 (lactic acid), EP A 432,610 (citric acid), and EP A 613,878 (citric acid). It is important to note that the purification of citric acid involves far fewer problems than the purification of lactic acid, as the fermentation is able to give rise to citric acid at a far higher concentration (about 40 percent by weight). In the fermentation to produce lactic acid, a concentration of about 30 percent by weight at most of calcium lactate (corresponding to about 21 per cent by weight of lactic acid) can be achieved.

WO 95/32301 describes a method of continuous preparation of an organic acid or the salt thereof, in the course of which fermentation in a bioreactor produces an aqueous acidic solution which is passed over an anion exchanger. The acid is released from the column by the column being treated with an alkali metal hydroxide.

WO 93/06226 describes a fermentation for producing lactic acid, in which a fermentation product is obtained which mainly contains undissociated lactic acid. The lactic acid is recovered by the fermentation product being brought into contact with a solid polymer containing pyridine groups, the acid being absorbed by the polymer.

WO 93/00440 describes a method of preparing lactic acid esters and lactic acid from a fermentation product, which involves the simultaneous reaction of a strong acid, an alcohol and a concentrated fermentation product which mainly contains lactate, and the removal of an azeotropic mixture of water and alcohol. The esters are purified by means of filtration and distillation.

U.S. Pat. No. 5,132,456 describes a method for recovering a carboxylic acid such as lactic acid from an aqueous composition having a pH which is close to the $pK_a$ of the acid, which involves purification of the acid by means of an anion exchanger.

U.S. Pat. No. 5,510,526 describes a method of preparing lactic acid from a lactate-containing feed by means of extraction, which involves the feed being brought into contact, under partial carbon dioxide pressure of at least 50 psi(g) (about 3.5 bar) with a water-immiscible amine which contains at least 18 carbon atoms, so that the acid is taken up in the organic amine phase. The acid is released again by means of back extraction.

U.S. Pat. No. 5,766,439 describes a method of preparing an organic acid such as lactic acid by fermentation, which involves an aqueous solution of the salt of the acid being formed. The salt is converted into an ammonium salt from which the acid is subsequently obtained.

EP A 159,585 describes a method of preparing lactic acid, in the course of which—after fermentation and acidification—lactic acid is directly subjected, ie. without a filtration step to remove solids, to an extraction, preferably using an alcohol, in a special extraction column.

The methods described in the prior art of preparing and purifying lactic acid are unsatisfactory, however, since lactic acid is obtained at a relatively low yield. Moreover, the purity of the lactic acid obtained is inadequate for certain applications such as applications in pharmaceutical and cosmetic compositions, industrial applications such as in coating compositions for electronic components (for example chips) and environment-friendly applications (e.g. preparation of biodegradable polylactic acid).

SUMMARY OF THE INVENTION

It is therefore an object of the present invention to provide a method by means of which lactic acid can be prepared efficiently and very cleanly. The invention therefore relates to a continuous process for preparing lactic acid, wherein the process comprises the following steps of:

(a) acidifying an aqueous feed [1], which has been obtained by fermentation and mainly contains lactate, with a stream [2] containing inorganic acid to a pH of from 1 to 4, preferably from 1.5 to 3 and especially from 1.7 to 2.3, to form an aqueous stream [3] which mainly consists of lactic acid and a salt, (b) removing the salt from the aqueous stream [3] which mainly contains lactic acid and salt by means of filtration (or decanting) to form a first aqueous stream [4] which mainly contains lactic acid, (c) passing the first aqueous stream [4] which mainly contains lactic acid over a column containing activated carbon to form a second aqueous stream [5] which mainly contains lactic acid, (d) subjecting the second aqueous stream [5] which mainly contains lactic acid to a first extraction step, wherein the second aqueous stream [5] which mainly contains lactic acid is brought into contact with a substantially water-insoluble stream [6] which contains an extractant, to form an organic phase [7] which mainly contains lactic acid and extractant and a first water phase [8] which mainly contains impurities, (e) subjecting the organic phase [7] which mainly contains lactic acid and extractant to a second extraction step, wherein the organic phase [7] which mainly contains lactic acid and extractant is brought into contact with an aqueous stream [9] to form a water phase [10] which mainly contains lactic acid and an organic phase [11] which mainly contains extractant, wherein the organic phase [11] which mainly contains extractant is recycled to step (d), and (f) concentrating the water phase [10] which mainly contains lactic acid by means of evaporation of water to form a concentrated lactic acid solution in water [12].

As already stated, the term "a feed which mainly contains lactate" relates to a feed which contains about 250 g of lactate ion/l or less, based on the total amount of the feed, at least 90 wt % of the lactate ion being present as free lactate ion and the remaining amount of the lactate ion being present as undissociated acid. It will, however, be evident to those skilled in the art that other lactic acid- and/or lactate-containing aqueous solutions can be purified using the method according to the invention. Thus it will be possible for a solution which mainly contains lactic acid to be purified by carrying out only the steps (c)–(f).

DESCRIPTION OF THE PREFERRED EMBODIMENT

Figure 1:
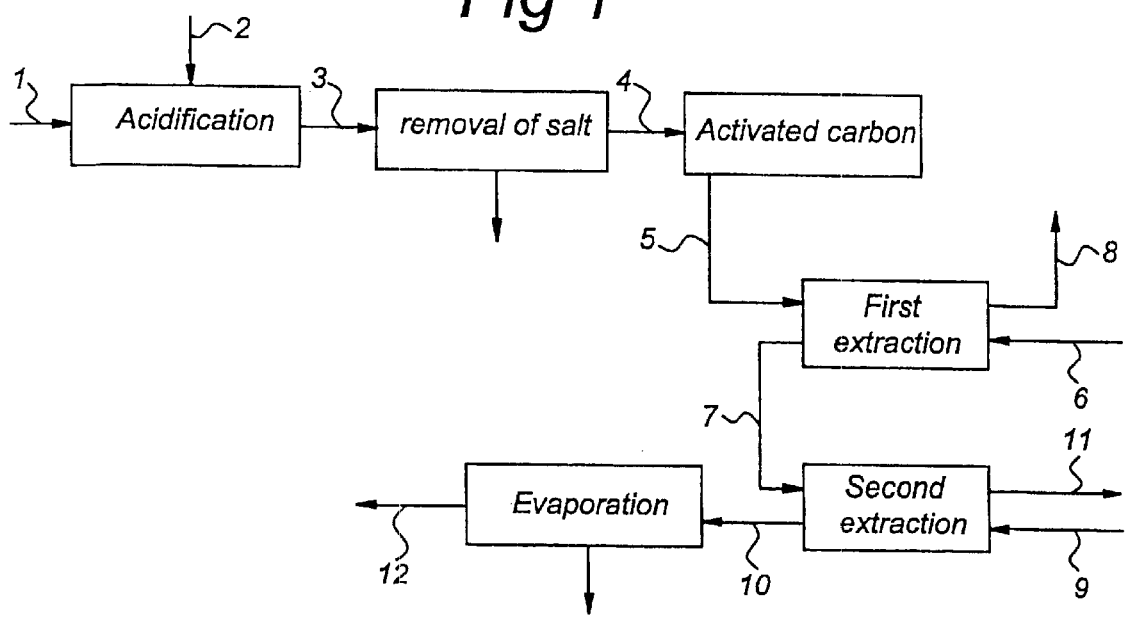
FIG. 1 depicts the process according to the invention.

According to FIG. 1, an aqueous feed [1] which mainly contains lactate is acidified with the stream [2] which contains inorganic acid, to form a stream [3] which mainly contains lactic acid and salt. Then the salt is removed to form the first aqueous stream [4] which mainly contains lactic acid and salt. This aqueous stream [4] is purified by passing it over a column which contains activated carbon, to form the second stream [5] which mainly contains lactic acid. Stream [5] undergoes a first extraction, stream [6] containing the extractant. Thus the lactic acid is extracted from the water phase to the organic phase (stream [7]), the water phase mainly containing impurities and a small amount of lactic acid (stream [8]). Stream [7] is subjected to a second extraction to form a water phase which mainly contains lactic acid (stream [10]) and an organic phase which mainly contains extractant (stream [11]). Finally, stream [10] is concentrated by evaporation of water, the concentrated lactic acid solution in water [12] being formed in the process.

Figure 2:
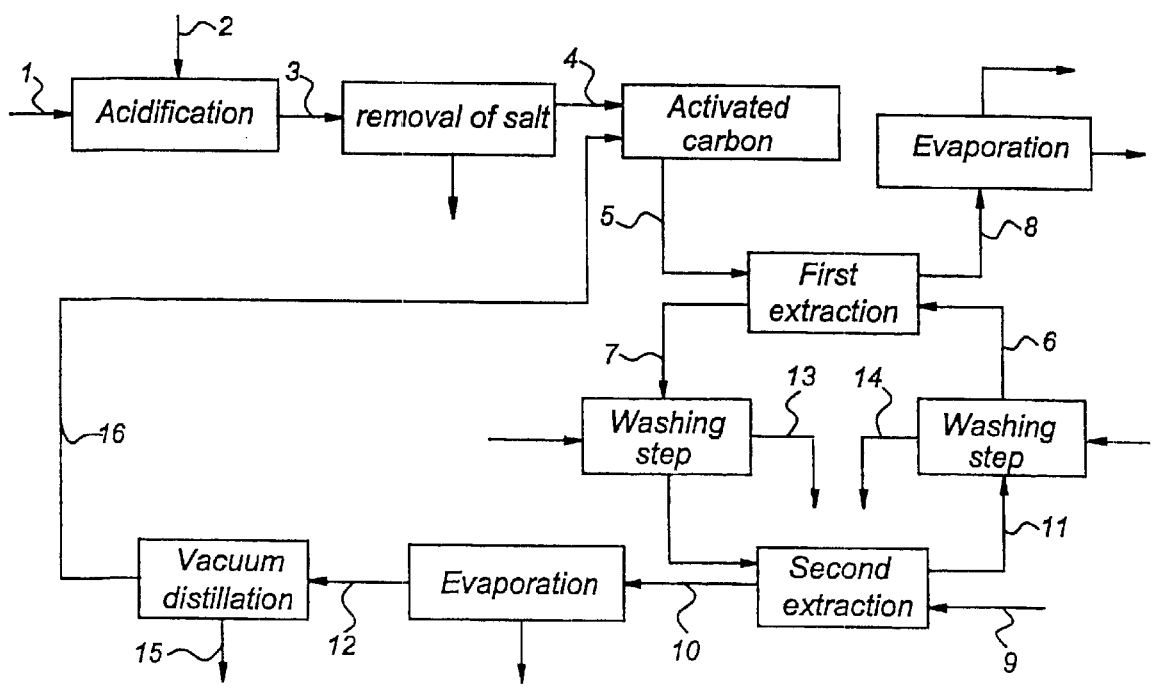
FIGS. 2 and 3 depict preferred embodiments of the process according to the invention.

According to FIG. 2, stream [7] is subjected to a washing step using water, in the course of which water-soluble impurities still remaining are removed from the lactic acid-containing organic phase, as described below in more detail. In this washing step it is inevitable that a small amount of lactic acid is washed out from the organic phase (stream [7]) at the same time, so that stream [13] is preferably recycled into the process, preferably upstream of step (c) or upstream of step (d), in particular upstream of (c). Furthermore, the mainly extractant-containing organic phase formed after the second extraction (stream [11]) is preferably washed with an aqueous solution of an inorganic base of an alkali metal, preferably sodium hydroxide, in order to remove any acid still present and other impurities from stream [11]. The stream thus purified [11] can again be employed for the first extraction, i.e. be used as a feed for [6]. In the course of the purification of stream [11], an aqueous stream [14] is released which is discharged as a waste stream. Furthermore, the concentrated lactic acid solution [12] is preferably distilled in vacuo, to form a substantially pure lactic acid (stream [15]) and a residue which, after possible further processing such as a depolymerization step, is recycled into the process, preferably upstream of step (c). Preferably, however, stream [12] is further purified prior to the vacuum distillation, preferably by passing it successively over a column which contains activated carbon and over an ion exchanger. In particular, stream [12] is passed over a column which contains activated carbon and then over an ion exchanger and is finally subjected to the vacuum distillation. According to the invention it is preferable, in particular, for stream [12] to be passed over (a) a column which contains activated carbon and (b) over an ion exchanger, after which the lactic acid-containing solution is further concentrated, using one or more falling-film evaporators, lubricated-film evaporators and/or thin-film evaporators, in conjunction or not in conjunction with one or more distillation columns, in order then to be distilled in vacuo to form highly pure lactic acid. In this embodiment, stream [12] will contain not more than 50 wt % of lactic acid, based on the total amount of the stream [12], as it was found that the ion exchanger is difficult to operate at higher concentrations of lactic acid. Then, the lactic acid-containing solution, having left the ion exchanger, will be further concentrated, in particular, by using one or more falling-film evaporators, lubricated-film evaporators and/or thin-film evaporators, in conjunction or not in conjunction with one or more distillation columns, before being distilled in vacuo. All these specific additional purification steps and their advantages will be discussed below in more detail.

Figure 3:
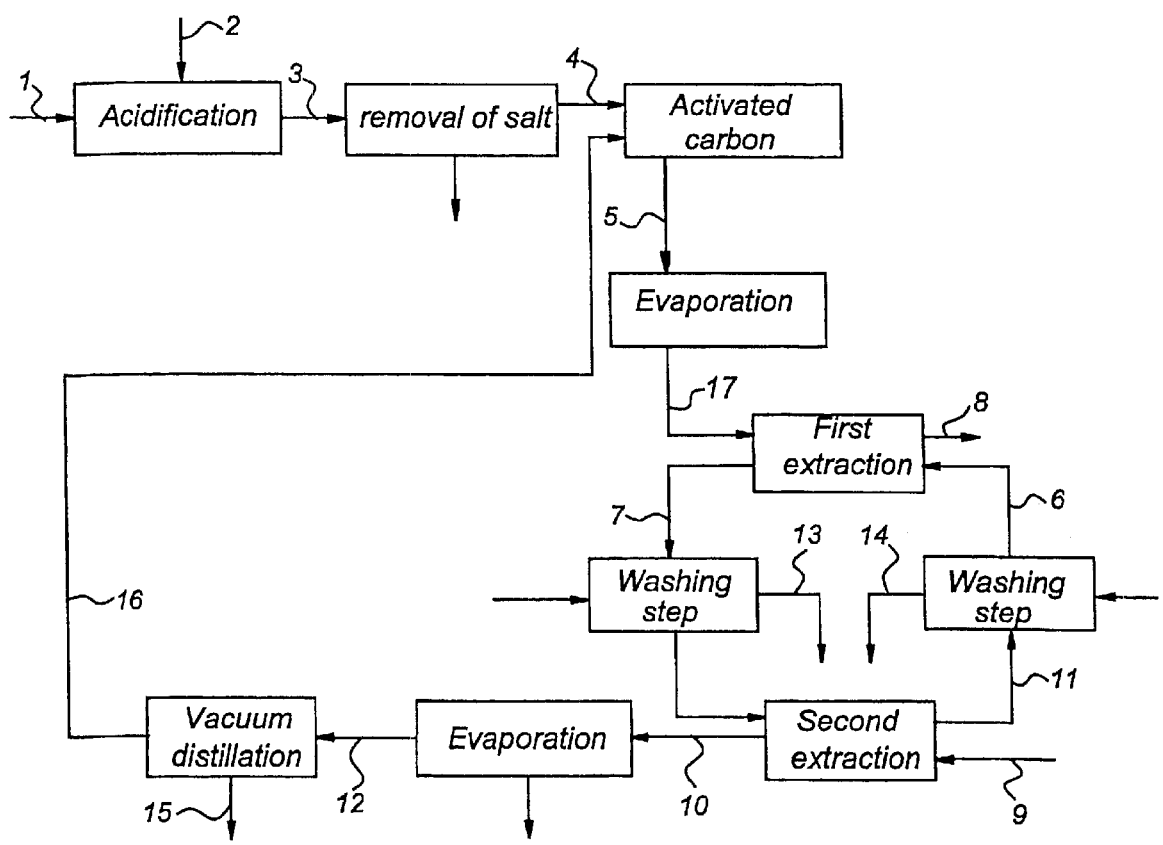

FIG. 3 depicts another preferred embodiment, in which stream [5] is subjected to an evaporation step. This evaporation step is carried out at a pressure of from atmospheric pressure to a pressure of 0.1 bar, in particular from 0.8 to 0.2 bar and at a temperature of from 25° to 140° C., more preferably from 40° to 100° C. and in particular from 50° to 90° C. This evaporation step gives rise to a concentrated stream [17] which contains from 30 to 50 wt % of lactic acid, based on the total amount of the stream [17]. Stream [17] is then fed to the first extraction step, a stream [8] being formed which contains at least 99.5 wt % of water and which can be discharged without further purification or treatment. Instead of stream [5], stream [4] can be subjected to this evaporation step.

Advantages of the present invention are that lactic acid can be obtained with high purity and with a high yield per unit weight of supplied feed per unit time. It is found, moreover, that the continuous process according to the present invention allows lactic acid to be produced with an efficiency which is at least double and even four times the efficiency implemented with a feed which has been obtained by a fermentation carried out at a pH of 4.8 or less, as described in WO 99/19290. Furthermore, the continuous process according to the present invention allows lactic acid to be obtained with a colour (after heating for 2 hours under reflux) of not more than 50 APHA, preferably not more than 25 APHA and, in particular, not more than 10 APHA (these values apply to lactic acid containing 92 wt % of pure lactic acid). The process according to the present invention can also be operated at lower cost than the known processes from the prior art, in particular because the costs of discharging the salt formed in step (a) and the procurement costs of the inorganic acid used in step (a) are considerably lower than the investment costs for extraction equipment which is able to operate under elevated pressure, for example extraction equipment necessary to carry out the process according to U.S. Pat. No. 5,510,526. Yet another advantage of the present invention is that the first extraction step (d) can be carried out under atmospheric pressure. A further advantage of operating at atmospheric pressure in the case of the extraction is a short response time (the system rapidly reaches equilibrium), which means that the method can be readily monitored and readily controlled and is less fault-prone. Furthermore, scaling up the methods to a large-scale industrial process is easier. Finally, the extraction is simpler than corresponding extractions known from the prior art, since only liquid/liquid systems are involved.

Preferably, the fermentation is carried out at a pH of from 5.2 to 7.0, the pH being maintained, by the addition of an inorganic base, to a value in the range of from 5.2 to 7.0. Also, upstream of step (a), the mainly lactate-containing aqueous mixture is preferably filtered to remove the biomass, in other words, upstream of step (a) the mainly lactate-containing aqueous feed [1] is filtered. It will be, evident to those skilled in the art that the biomass can also be separated in other known ways, for example by decanting.

The salt formed in step (a) is composed of an anion of the inorganic acid and a cation of the inorganic base, as shown by the following example of the acidification step:

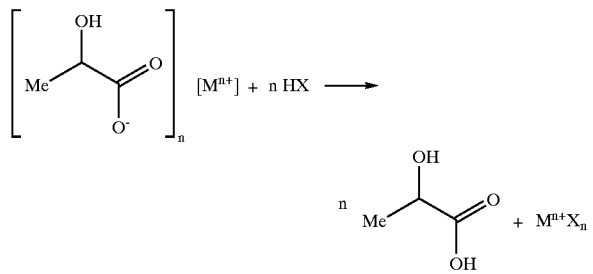

The aqueous stream [8] which is formed during the first extraction step (forward extraction) preferably contains at least 90 wt % of water, based on the mixture in total, and in particular at least 95 wt % of water. Moreover, stream [8] preferably contains not more than 5 wt % of lactic acid. For efficacious extraction, stream [8] is therefore recycled into the process upstream of step (c) or upstream of step (d), in particular upstream of step (c). In both cases, it will often be necessary to introduce a "purge" before said stream [8] is recycled into the process, in order to prevent accumulation of impurities. Furthermore, the first water phase [8] which mainly contains impurities is concentrated by means of evaporation of water, before said stream undergoes further processing, either as a waste stream or as a recycle stream.

According to another preferred embodiment according to the invention, concentration of stream [8] can be omitted. In this case, a concentration step is carried out either upstream of step (c) or upstream of step (d), either stream [4] or stream [5] being concentrated so as to give rise to a concentrated, lactic acid-containing stream which contains from 30 to 50 wt % of lactic acid, based on the total amount of the stream. This concentrated, lactic acid-containing aqueous stream is then subjected to the first extraction step, giving rise to a stream [8] which mainly contains only water (at least 99.5 wt % of water), so that this stream can be discharged directly, i.e. without further purification.

Preferably, the organic phase [7] which mainly contains lactic acid and extractant is subjected, upstream of step (e), to a washing step with water to form a second water phase [30] which mainly contains impurities. As stream [13] still contains lactic acid, this stream is preferably recycled into the process according to the invention, preferably upstream of step (c) or upstream of step (d) and in particular upstream of step (c).

The organic phase [11] which mainly contains extractant is recycled, possibly in part but preferably in total, to the first extraction step. Thus the extractant is expediently recirculated during the process. It is preferable for this stream [11] to be subjected to a washing step using an aqueous solution of an inorganic base, preferably an aqueous solution of an alkali metal hydroxide such as sodium hydroxide, to form water phase [14]. This stream [14] is discharged as a waste stream.

Step (a) of the method according to the invention is preferably carried out at atmospheric pressure under a temperature of from 20° to 100° C., more preferably at a temperature of from 40° to 90° C. and in particular at a temperature of from 50° to 80° C. The inorganic acid used in step (a) preferably has an anion which forms a substantially water-insoluble salt with the cation of the inorganic base used in the fermentation. That means that $M^{n+}X_n$ in the above-shown reaction equation is a salt which is barely soluble or substantially insoluble in water.

The inorganic base used in the fermentation is preferably an alkaline earth metal carbonate, an alkaline earth metal hydrogencarbonate, an alkaline earth metal hydroxide or an alkaline earth metal oxide the alkaline earth metal forming a substantially water-insoluble salt with the anion of the acid which is used in step (a) and preferably being calcium or magnesium. In particular, the inorganic base is calcium carbonate or calcium hydroxide.

According to the invention, the inorganic acid used in step (a) is preferably sulphuric acid, and the base used in the fermentation, in particular, is a calcium base. In that case, calcium sulphate is formed upon acidification.

Step (b) of the method according to the invention is preferably carried out at atmospheric pressure and ambient temperature. Optionally, the salt is dried after step (b), in particular if step (a) was not carried out at elevated pressure. The salt can be removed by filtration or decanting or some other comparable technique from the aqueous stream [3] which mainly contains lactic acid and salt.

If it is desirable for drier crystals to be prepared in step (b), step (a) is preferably carried out at a pressure of from 5 to 10 bar, in particular a pressure of from 6 to 8 bar, and a temperature of 100° C., in particular a temperature of 100° and 120° C. If the salt is calcium sulphate this has the advantage that the drier calcium sulphate crystals can be used directly for various other purposes, for example in the fabrication of gypsum board and porcelain.

Step (c) of the method according to the invention is preferably carried out at atmospheric pressure under a temperature of from 50° to 70° C., in particular at a temperature of from 55° to 65°C. From 0.1 to 5 g of activated carbon per liter of lactic acid is preferably used in the column containing activated carbon.

Step (d) of the method according to the invention is preferably carried out at atmospheric pressure and at a temperature of from 0° to 60° C., in particular at a temperature from 10° to 50° C. If the extractant does not contain an alcohol and/or ketone, step (d) is preferably carried out, however, at atmospheric pressure and a temperature of 60° to 100° C. The volume ratio of the second aqueous stream [5] which mainly contains lactic acid (or of [17]) and the substantially water-insoluble stream [6] which contains the extractant is preferably between 20:1 and 1:20, more preferably between 3:1 and 1:7, and in particular between 2:1 and 1:5.

The extractant used in step (d) of the method according to the invention preferably comprises an (1) amine and (2) a hydrocarbon. Preferably, the extractant also comprises (3) an alcohol and/or a ketone. As noted, the conditions at which step (d) of the method according to the invention is carried out will vary. If the extractant does not contain an alcohol and/or ketone, step (d) is preferably carried out at atmospheric pressure and a temperature of from 60° to 100° C. In the other case, step (d) is preferably carried out at atmospheric pressure and at a temperature of from 0° to 60° C., in particular at a temperature of from 10° to 50° C. The amine is preferably a tertiary amine having at least 18 carbon atoms and preferably contains from 24 to 42 carbon atoms. If the extractant contains an alcohol, which is preferred, the alcohol is a $C_8$–$C_{12}$ alcohol, the alcohol being optionally linear or branched and preferably being a branched alcohol. The hydrocarbon is preferably a petroleum fraction which consists of saturated alkanes, and preferably has a flashpoint of at least 40° C., more preferably at least 70° C. and in particular a flashpoint of at least 90° C. A higher flashpoint has the advantage that the safety requirement imposed on the equipment used in step (e) need not be as severe. The boiling range of the hydrocarbon is preferably from 150 to 275° C., in particular from 170 to 260° C. The hydrocarbon, in particular, is Isopar K™ or Isopar M™. The extractant preferably contains from 40 to 75 wt % of (1), from 5 to 60 wt % of (2) and from 0 to 25 wt % of (3), and in particular from 45 to 60 wt % of (1), from 40 to 55 wt % of (2) and from 0 to 10 wt % of (3).

The volume ratio of the organic phase [7] which mainly contains lactic acid and extractant, and the aqueous stream [9]-step (e)—is preferably between 20:1 and 1:20, more preferably between 3:1 and 1:7 and in particular between 2:1 and 1:5, and especially between 1:2 and 1:4.

Step (e) of the method according to the invention is preferably carried out at a pressure of from 1 to 10 bar, in particular at a pressure from 2 to 9 bar, and a temperature of from 100° C. to 180° C., in particular a temperature of from 120° to 160° C.

Step (f) of the method according to the invention is preferably carried out in one or more falling-film evaporators and/or thin-film evaporators and/or lubricated-film evaporators, step (f) preferably being carried out at atmospheric pressure to a pressure of 0.1 bar, in particular from 0.8 to 0.2 bar, and at a temperature of from 25° to 140° C., more preferably of from 40° to 100° C. and in particular from 60° to 85° C. In the process, stream [10] is preferably subject to a pressure of from 0.5 to 1 bar, in particular of from 0.7 to 0.9 bar, and a temperature of from 50° to 100° C., in particular of from 70° to 90° C.

According to the invention it is preferable for the concentrated lactic acid solution in water [12] to be distilled in vacuo to form lactic acid [15] and a distillation residue [16], stream [12] containing at least 95 wt % and preferably from 99 to 99.9 wt % of lactic acid and stream [15] containing at least 99.5 wt % of lactic acid. For the purpose of the invention, vacuum is to be understood as a pressure in the range of from 0.1 to 20 mbar, in particular of from 2 to 10 mbar. The temperature during the vacuum distillation is preferably from 100 to 200° C., preferably from 110 to 140° C.

According to another preferred embodiment of the invention, the concentrated lactic acid solution [12] is preferably subjected to a first and a second distillation step. The first distillation step is preferably carried out at a temperature of from 80° to 150° C., in particular at a temperature of from 100° to 140° C., and at a pressure of from 50 to 250 mbar, in particular a pressure of from 60 to 150 mbar. The first distillation step is preferably carried out in such a way that the solution is converted into the vapour phase by means of film evaporation and the vapour is passed to a first distillation column. In the process, with reflux, separation into two fractions occurs, the top fraction containing water and at most 1 wt % of lactic acid, preferably at most 0.1 wt % of lactic acid, and the bottom fraction containing from 95 to 100 wt % of lactic acid, preferably from 99 to 100 wt % of lactic acid. The film evaporation preferably takes place by means of lubricated-film evaporation, thin-film evaporation and/or falling-film evaporation, the distillation column or columns having a number of theoretical trays of from 1 to 10. The product obtained from the first distillation step contains at least 95 wt % of lactic acid, based on the total weight of the product.

Then the product obtained from the first distillation step is subjected, in a second distillation step, to a vacuum distillation which is preferably carried out at a pressure of from 0.1 to 20 mbar, in particular from 2 to 10 mbar, and at a temperature of from 100° to 200° C., in particular a temperature of from 110° to 140° C. In the second distillation step, the product of the first distillation step is transferred into the vapour phase, preferably by means of film evaporation, and the vapour is then passed to a second distillation column. Here, again, separation into two fractions takes place under reflux, the top fraction containing at least 99.5 wt % of lactic acid and the residue containing sugars other than lactic acid. In a second distillation step, the film evaporation preferably takes place by means of lubricated-film evaporation, thin-film evaporation and/or falling-film evaporation, the distillation column or columns preferably having a number of theoretical trays of from 1 to 10.

According to the invention it is preferable, in particular, for the product of the first distillation step to be subjected to a conditioning step (a so-called "preflash"), in which the pressure is preferably equal to that of the second distillation. The pressure may, however, alternatively be higher by 100%, i.e. at most 40 mbar. This preferred embodiment has the advantage that a further small amount of water is removed prior to the product being subjected to the second distillation step. In general, the separated water phase contains from 10 to 20 wt % of lactic acid.

If a stream [12] which contains not more than 50 wt % of lactic acid, based on the total amount of stream [12] has been passed over a column which contains activated carbon and then over an ion exchanger, said stream [12] is concentrated using one or more lubricated-film evaporators, thin-film evaporators and/or falling-film evaporators, optionally in conjunction with one or more distillation columns having a number of theoretical trays of from 1 to 10, before said stream [12] is subjected to the conditioning step. In the course of this concentration, a stream is obtained which contains at least 98 wt % of lactic acid, based on the total amount of the stream. Said concentration is carried out at a pressure of from 0.5 to 0.8 bar and at a temperature of from 65° to 150° C.

The distillation residue [16] is recycled into the process, preferably either upstream of step (c) or upstream of step (d), or to the first distillation step, in particular upstream of step (c). If distillation residue [16] is recycled into the process upstream of step (c) or upstream of step (d) a sink is required.

The distillation residue [16] is preferably subjected to a depolymerization step before said residue is recycled into the process, in particular because the residue contains oligomers of lactic acid.

The depolymerization is preferably carried out by a mixture of from 30 to 70 wt %, preferably from 40 to 60 wt %, of an aqueous stream which preferably contains from 80 to 100 wt % of water, and of from 70 to 30 wt %, preferably from 60 to 40 wt %, of the residue of the second distillation step being heated for from 1 to 10 hours under atmospheric pressure at a temperature of from 60° to 100° C. This aqueous stream preferably stems from the first distillation and/or "preflash".

The invention also relates to a concentrated lactic acid solution in water [12] obtainable in accordance with the continuous process according to the invention. The invention further relates to lactic acid obtainable in accordance with the continuous process according to the invention, in particular to lactic acid having a colour (after heating for 2 hours under reflux) of preferably not more than 25 APHA units, in particular not more than 10 APHA units. If the continuous process also comprises a first and second distillation step of the concentrated lactic acid solution [12], in which said solution has been passed over a column which contains activated carbon and then over an ion exchanger, the invention further relates to lactic acid which has not more than 60 APHA units, preferably not more than 40 APHA units and in particular not more than 5 APHA units (after heating for 2 hours under reflux).

EXAMPLE

1. Preparation of the Impure Lactic Acid Solution

A quantity of 7 liters of an aqueous feed, which had been obtained by fermentation carried out at a pH of 6.4 and contained 13 percent by weight of calcium lactate, was acidified, over a period of about 45 minutes, with sulphuric acid to a pH of 2.0 at a temperature of from about 72° to 75° C. Then the mixture obtained was filtered over a Büchner filter (S&S 595 filters), for the purpose of separating off calcium sulphate. The calcium sulphate had the properties as shown in Table 1.

TABLE 1

| Impurities | Amount (ppm) |
| --- | --- |
| Chloride | <40 |
| Silicon | <200 |
| Potassium | 28 |
| Sodium | 45 |
| Arsenic | <3 |
| Cadmium | 0.5 |
| Chromium | <3 |
| Copper | <3 |
| Iron | <50 |
| Magnesium | <20 |
| Nickel | <2 |
| Lead | <3 |

TABLE 1-continued

| Impurities | Amount (ppm) |
| --- | --- |
| Zinc | <10 |
| Phosphorus | 62 |
| Mercury | 0.09 |

2. Treatment with Activated Carbon

Activated carbon was rinsed with deionized water. Two 75 ml columns were used which contained activated carbon. The temperature in the columns was maintained at 60° C. A quantity of 4 liters of the impure lactic acid solution was then passed over the columns at a rate of 5 bed volumes per hour, the first 5 bed volumes of product being kept apart; the remainder was used for the extraction trials.

3. Extraction

Preparation of the Extractant

Two extractants were used for the trial: (a) an extractant which contained 48:30:22 (expressed in percent by weight, based on the total amount of the extractant) of Alamine 336™, 1-octanol and Isopar K™, and (b) an extractant which contained 48:7:45 (expressed in percent by weight, based on the total amount of the extractant) of Alamine 336™, 1-octanol and Isopar K™. Alamine 336™ was washed beforehand with a solution of 4% by weight of sodium hydroxide in water, in a volume ratio of 1:1, and then with deionized water until the pH of the water phase was less than 9.0. Then, Alamine 336™ was mixed with the other components.

First Extraction Step

These trials were carried out in quintuplicate with both extractants (a) and (b). The ratio of organic phase to aqueous phase was 1:1, the two phases being mixed for 120 seconds using a stirrer speed of from 300 to 450 rpm. The mixing was carried out in a mixing apparatus fitted with a stationary twin-blade stirrer of the type Cole-Palmer P-06367-10. A 600 ml vessel (diameter 8 cm) was charged with 150 ml of extractant. Then 150 ml of the non-purified lactic acid solution as obtained in step 2 were added, and the mixture was stirred for 120 seconds. Then the mixture was allowed to separate at ambient temperature into two phases, the time required being measured.

Second Extraction Step

These trials were carried out in an autoclave at 120° C., 350 ml of deionized water and 500 ml of the mixture of lactic acid and extractant as obtained in the previous step being introduced into the autoclave. The mixture was stirred at 50 rpm and 120° C., a time of about 1 hour being required to raise the temperature from ambient temperature to 120° C. When the temperature was 120° C., the stirring speed was raised from 50 to 300 rpm. After about 10 minutes, stirring was stopped and the phases were allowed to separate for about 10 minutes. Then samples were taken of both phases and the content of the autoclave were allowed to cool to ambient temperature.

Analysis

All the samples were analysed for their content of lactic acid, other organic acids, total nitrogen, amino acids, octyl lactate, cations, anions, sulphate, phosphate, furans, polyfurans, colour (prior to heating), colour (after heating), residual sugars and polysaccharides. The data are shown in the following table. The streams are as follows: (A) stream [1], (B) stream [4], (C) stream [5], (D) stream [10], (E)

stream [8], (F) stream [7] and (G) stream [11]. The trials with (D1)–(G1) were carried out using an extractant which contained Alamine 336™, 1-octanol and Isopar K™ with a weight ratio of 48:30:22, while the trials with (D2)–(G2) were carried out using an extractant which contained Alamine 336™, 1-octanol and Isopar K™ with a weight ratio of 48:7:45.

tion at a pH of from 5.2 to 7.0, the pH being maintained at a value in the range of from 5.2 to 7.0 by the addition of an inorganic base.

3. Process according to claim 1, wherein step (a) is preceded by the aqueous feed [1] which mainly contains lactate being filtered or decanted.

TABLE 2

| Component | (A) | (B) | (C) | (D1) | (E1) | (F1) | (G1) | (D2) | (E2) | (F2) | (G2) |
|---|---|---|---|---|---|---|---|---|---|---|---|
| Lactic acid (wt %) | 17.8 | 17.3 | 17.5 | 5.8 | 12.0 | 8.8 | 3.3 | 7.4 | 11.5 | 9.1 | 2.9 |
| Org. acid (wt %) | <0.3 | <0.3 | <0.3 | <0.1 | <0.1 | >0.3 | <0.1 | <0.2 | <0.1 | 0.4 | <0.3 |
| $N_{tot}$ (ppm) | 255 | 395 | 260 | 30 | 300 | — | — | <20 | 240 | — | — |
| Amino acids (mM) | 12.7 | 13.0 | 12.8 | 0.4 | 15.1 | — | — | 0.4 | 15.0 | — | — |
| $C_8$-La (ppm) | — | — | — | 3.3 | <1 | 1500 | 550 | 3.5 | <1 | 600 | 330 |
| Cations (ppm) | 17117 | 14491 | 14335 | <64 | 16876 | — | — | <95 | 16974 | — | — |
| Anions (ppm) | — | >50000 | >50000 | <515 | >25000 | — | — | <515 | >25000 | — | — |
| Sulphate (ppm) | — | >50000 | >50000 | 500 | 25000 | — | — | 1000 | 25000 | — | — |
| Phosphate (ppm) | — | <5 | <5 | <5 | <5 | — | — | <5 | <5 | — | — |
| Colour (prior to heating; APHA) | 1500 | 3130 | 320 | 63 | 380 | — | — | 100 | 380 | — | — |
| Colour (after heating; APHA) | 1650 | 4190 | 790 | 67 | 590 | — | — | 175 | 555 | — | — |
| Residual sugars (mg/l) | 394 | 388 | 363 | <2.9 | 474 | — | — | <5.0 | 466 | — | — |
| Polysaccharides (mg/l) | 710 | 813 | 870 | 13.6 | 654 | — | — | 20 | 754 | — | — |

What is claimed is:

1. Continuous process for preparing lactic acid, wherein the process comprises the following steps:
   (a) acidifying an aqueous feed [1], which has been obtained by fermentation and mainly contains lactate, with a stream [3] which mainly consists of lactic acid and a salt,
   (b) removing the salt from the aqueous stream [3] which mainly contains lactic acid and salt by means of filtration to form aqueous stream [4] which mainly contains lactic acid,
   (c) passing aqueous stream [4] which mainly contains lactic acid over a column containing activated carbon to form aqueous stream [5] which mainly contains lactic acid,
   (d) subjecting aqueous stream [5] which mainly contains lactic acid to a first extraction step, wherein aqueous stream [5] which mainly contains lactic acid is brought into contact with a substantially water-insoluble stream [6] which contains an extractant, to form a an organic phase [7] which mainly contains lactic acid and extractant and a first water phase [8] which mainly contains impurities,
   (e) subjecting the organic phase [7] which mainly contains lactic acid and extractant to a second extraction step, wherein the organic phase [7] which mainly contains lactic acid and extractant is brought into contact with an aqueous stream [9] to form a water phase [10] which mainly contains lactic acid and an organic phase [11] which mainly contains extractant, wherein the organic phase [11] which mainly contains extractant is recycled to step (d), and
   (f) concentrating the water phase [10] which mainly contain contains lactic acid by means of evaporation of water to form a concentrated lactic acid solution in water [12].

2. Process according to claim 1, wherein the aqueous feed [1] which mainly contains lactate is prepared by fermenta- 4. Process according to claim 1, wherein first water phase [8] contains at least 90 wt % of water, based on the mixture in total.

5. Process according to claim 4, wherein the aqueous stream contains at least 95 wt % of water.

6. Process according to claim 1, wherein the organic phase [7] which mainly contains lactic acid and extractant is subjected, upstream of step (e), to a washing step with water to form a second water phase [13] which mainly contains impurities.

7. Process according to claim 6, wherein the second water phase [13] which mainly contains impurities is recycled into the process upstream of step (c).

8. Process according to claim 1, wherein the organic phase [11] which mainly contains extractant is recycled, or partly recycled, to the first extraction step.

9. Process according to claim 1, wherein the first water phase [8] which mainly contains impurities is concentrated by means of evaporation of water.

10. Process according to claim 1, wherein the first water phase [8] which mainly contains impurities is partly recycled into the process upstream of step (c).

11. Process according to claim 1, wherein the second stream [5] which mainly contains lactic acid is subjected to an evaporation step.

12. Process according to claim 11, wherein the evaporation is carried out at a pressure of from atmospheric pressure to a pressure of 0.1 bar and at a temperature of from 25° to 140° C.

13. Process according to claim 11, wherein stream [5] is concentrated to produce a concentrated stream which contains from 30 to 50 wt % of lactic acid.

14. Process according to claim 1, wherein the first stream [4] which mainly contains lactic acid is subjected to an evaporation step.

15. Process according to claim 14, wherein the evaporation is carried out at a pressure of from atmospheric pressure to a pressure of 0.1 bar and at a temperature of from 25° to 140° C.

16. Process according to claim 14, wherein stream [4] is concentrated to produce a concentrated stream which contains from 30 to 50 wt % of lactic acid.

17. Process according to claim 13, wherein the concentrated stream [17] is subjected to the first extraction step.

18. Process according to claim 16, wherein the concentrated stream is passed over a column which contains activated carbon to form a second aqueous stream [5] which mainly contains lactic acid.

19. Process according to claim 1, wherein the aqueous feed [1] which mainly contains lactate has a pH in the range from 5.2 to 7.0 and contains from 0.1 to 250 g of lactate ion per liter, based on the total amount of the mixture.

20. Process according to claim 1, wherein step (a) is carried out at atmospheric pressure and a temperature of 20° C. to 100° C.

21. Process according to claim 20, wherein the temperature is between 40° and 90° C.

22. Process according to claim 20, wherein the temperature is between 50° and 80° C.

23. Process according to claim 1, wherein step (a) is carried out at a pressure of from 5 to 10 bar and a temperature of 100° C or more.

24. Process according to claim 23, wherein the temperature is between 100° and 120° C.

25. Process according to claim 1, wherein step (b) is carried out at atmospheric pressure and at ambient temperature.

26. Process according to claim 1, wherein the salt is dried after step (b).

27. Process according to claim 1, wherein step (c) is carried out at atmospheric pressure and a temperature of from 50° to 70° C.

28. Process according to claim 27, wherein the temperature is between 55° and 65° C.

29. Process according to claim 1, wherein step (d) is carried out at atmospheric pressure and a temperature of from 0° to 60° C.

30. Process according to claim 29, wherein the temperature is between 10° and 50° C.

31. Process according to claim 1, wherein step (d) is carried out at atmospheric pressure and a temperature of from 60° to 100° C.

32. Process according to claim 1, wherein the volume ratio of the second aqueous stream [5] which mainly contained lactic acid or of stream [17] and the substantially water-insoluble stream [6] which contains the extractant is between 20:1 and 1:20.

33. Process according to claim 1, wherein step (e) is carried out at a pressure of from 1 to 10 bar and a temperature of from 100° C. to 180° C.

34. Process according to claim 33, wherein the pressure is between 2 and 9 bar.

35. Process according to claim 33, wherein the temperature is between 120° and 160° C.

36. Process according to claim 1, wherein the volume ratio of the organic phase [7] which mainly contains lactic acid and extractant and the aqueous stream [9] is between 20:1 and 1:20.

37. Process according to claim 1, wherein step (f) is carried out in one or more falling-film evaporators and/or thin-film evaporators and/or lubricated-film evaporators.

38. Process according to claim 1, wherein step (f) is carried out at from atmospheric pressure to a pressure of 0.1 bar and at a temperature of from 25° to 140° C.

39. Process according to claim 1, wherein the inorganic base is an alkaline earth metal carbonate, an alkaline earth metal hydrogencarbonate, an alkaline earth metal hydroxide or an alkaline earth metal oxide.

40. Process according to claim 39, wherein the alkaline earth metal is calcium or magnesium.

41. Process according to claim 39, wherein the inorganic base is calcium carbonate or calcium hydroxide.

42. Process according to claim 1, wherein the inorganic acid used in step (a) is sulphuric acid.

43. Process according to claim 1, wherein the extractant comprises (1) an amine and (2) a hydrocarbon.

44. Process according to claim 43, wherein the extractant comprises (3) an alcohol and/or a ketone.

45. Process according to claim 43, wherein the amine is a tertiary amine having at least 18 carbon atoms.

46. Process according to claim 45, wherein the amine contains from 24 to 42 carbon 10 atoms.

47. Process according to claim 44, wherein the extractant contains an alcohol.

48. Process according to claim 47, wherein the alcohol is a $C_8$–$C_{12}$ alcohol.

49. Process according to claim 47, wherein the alcohol is a branched alcohol.

50. Process according to claim 43, wherein the hydrocarbon is a petroleum fraction which consists of saturated alkanes.

51. Process according to claim 50, wherein the hydrocarbon has a flashpoint of at least 40° C.

52. Process according to claim 50, wherein the hydrocarbon has a flashpoint of at least 70° C. and a boiling range of between 150 to 275° C.

53. Process according to claim 44, wherein the extractant contains from 40 to 75 wt % of (1), from 5 to 60 wt % of (2) and from 0 to 25 wt % of (3).

54. Process according to claim 1, wherein the organic phase [11] which mainly contains extractant is subjected to a washing step with an aqueous solution of an inorganic base.

55. Process according to claim 1, wherein the water phase [10] which mainly contains lactic acid contains from 0.1 to 30 wt % of lactic acid.

56. Process according to claim 1, wherein the concentrated lactic acid solution in water [12] is distilled in vacuo to form lactic acid and a distillation residue.

57. Process according to claim 56, wherein the vacuum distillation is carried out at a pressure of from 0.1 to 20 mbar and a temperature of from 100 to 200° C.

58. Process according to claim 56, wherein the distillation residue [16] is recycled into the process upstream of step (c).

59. Process according to claim 1, wherein the vacuum distillation step is preceded by the concentrated lactic acid solution [12] being passed over a column which contains activated carbon.

60. Process according to claim 59, wherein the vacuum distillation step is preceded by the concentrated lactic acid solution [12] being passed over an ion exchanger.

61. Process according to claim 59, wherein the vacuum distillation step is preceded by the concentrated lactic acid solution [12] being passed over a column which contains activated carbon and then over an ion exchanger.

62. Process according to claim 61, wherein stream [12] contains not more than 50 wt % of lactic acid and after the treatment with the ion exchanger is concentrated to produce a stream which contains at least 98 wt % of lactic acid.

63. Process according to claim 62, wherein stream [12], after the concentration step and prior to the vacuum distillation, is subjected to a conditioning step.

64. Process according to claim 62, wherein the concentration is carried out at a pressure of from 0.5 to 0.2 bar and at a temperature of from 65° to 150° C.

* * * * *